United States Patent [19]

Yamamoto et al.

[11] Patent Number: 5,639,472
[45] Date of Patent: Jun. 17, 1997

[54] PERCUTANEOUS ABSORPTION PREPARATION

[75] Inventors: Keiji Yamamoto; Yoshihisa Nakano; Saburo Otsuka, all of Osaka, Japan

[73] Assignees: Nitto Denko Corporation, Osaka; Hokuriku Seiyaku Co., Ltd., Fukui, both of Japan

[21] Appl. No.: 419,181

[22] Filed: Apr. 10, 1995

[30] Foreign Application Priority Data

Apr. 14, 1994 [JP] Japan ................................. 6-75600

[51] Int. Cl.$^6$ ................................................ A61K 9/70
[52] U.S. Cl. .................. 424/449; 424/448; 514/728; 514/731; 514/741; 514/653
[58] Field of Search ........................... 514/728, 731, 514/741, 653; 424/448, 449

[56] References Cited

U.S. PATENT DOCUMENTS

| 5,176,916 | 1/1993 | Yamanaka et al. | 424/448 |
| 5,254,348 | 10/1993 | Hoffmann et al. | 424/449 |
| 5,312,627 | 5/1994 | Stroppolo et al. | 424/448 |

FOREIGN PATENT DOCUMENTS

| 0189861A2 | 8/1988 | European Pat. Off. |
| 0374980A2 | 6/1990 | European Pat. Off. |
| 0439180A3 | 10/1991 | European Pat. Off. |
| 0523537A1 | 1/1993 | European Pat. Off. |

OTHER PUBLICATIONS

Chemical Abstracts, vol. 120, No. 14, Apr. 4, 1994, Columbus, OH, US; Abstract No. 173510 corresponding to WO-A-94 02119 (Hisamitsu Pharmaceutical CO. Inc.) Feb. 3, 1994.

Database WPI, Week 8808, Derwent Publications, Ltd, London, GB; AN 88-053903 corresponding to JP-A-63 010 716 (Teijin KK) Jan. 18, 1988.

*Primary Examiner*—James J. Seidleck
*Assistant Examiner*—Michael A. Williamson
*Attorney, Agent, or Firm*—Sughrue, Mion, Zinn, Macpeak & Seas

[57] ABSTRACT

A percutaneous absorption preparation comprising a support and, formed on one side thereof, a plaster layer comprising a pressure-sensitive adhesive and tulobuterol in an amount not lower than its saturation solubility in the pressure-sensitive adhesive, the tulobuterol contained in the plaster layer consisting of dissolved tulobuterol and crystalline tulobuterol with the ratio of the content of the crystalline tulobuterol to that of the dissolved tulobuterol being from 0.1 to 10.

6 Claims, No Drawings

PERCUTANEOUS ABSORPTION PREPARATION

FIELD OF THE INVENTION

The present invention relates to a percutaneous absorption preparation which is applied to a skin surface to continuously administer tulobuterol to the living body through the skin. More particularly, this invention relates to a percutaneous absorption preparation which, when applied to a skin surface, shows excellent skin adhesive properties and maintains an effective blood level of tulobuterol over a prolonged period of time.

BACKGROUND OF THE INVENTION

Tulobuterol functions to selectively stimulate $\beta_2$-receptors of the sympathetic nerves to show a bronchodilatory action. This drug is widely used in the treatment of chronic bronchitis, bronchial asthma, and the like in order to relieve dyspnea of the patients suffering from air way stricture.

Generally employed methods for administering tulobuterol to the living body include oral administration in the form of tablets, dry syrup, etc. However, the oral administration has problems, for example, that administration to infants and the like is difficult, the blood level of the drug increases rapidly to produce severe side effects, and the efficacy duration is short. To overcome these problems, an adhesive preparation of tulobuterol is proposed as described in JP-A-4-99720 (the term "JP-A" as used herein means an "unexamined published Japanese patent application"). Adhesive preparations have an advantage that since the drug is percutaneously administered, administration to infants and like is easy and the drug is rapidly absorbed through the skin. Such preparations are also advantageous in that efficacy duration can be attained and side effects can be diminished.

In an adhesive preparation containing tulobuterol, the tulobuterol contained in the plaster layer, which comes into contact with a skin surface, is present in a crystalline state or dissolved state depending on the saturation solubility thereof in the plaster layer. When this adhesive preparation is applied to a skin surface, the tulobuterol in a dissolved state (hereinafter also referred to as "dissolved tulobuterol") speedily migrates to the skin and is absorbed as long as the dissolved tulobuterol is not trapped, e.g., by the pressure-sensitive adhesive contained in the plaster layer as a result of ionic bonding with functional groups of the adhesive, although the tulobuterol in a crystalline state (hereinafter also referred to as "crystalline tulobuterol") does not participate in percutaneous absorption. Hence, the higher the content of dissolved tulobuterol in the plaster layer, the larger the amount of percutaneously absorbed tulobuterol and the longer the efficacy duration. Consequently, investigations are usually directed to developments of adhesive preparations containing dissolved tulobuterol.

In other words, the above means that the pharmacologically-active-duration time for tulobuterol is limited by the saturation solubility of tulobuterol in the pressure-sensitive adhesive. Therefore, use of a pressure-sensitive adhesive in which tulobuterol has a low solubility poses a problem that an effective blood level of tulobuterol cannot be maintained for a sufficiently long time period.

For obtaining a satisfactory efficacy duration, it is necessary to administer the drug in an increased amount, for example, by increasing the thickness of the plaster layer containing tulobuterol dissolved therein, by heightening the content of tulobuterol, or by enlarging the area in which the plaster layer is in contact with the skin. However, these expedients pose the following problems: the patient comes to have an enhanced uncomfortable application feeling and the skin irritation is increased; the plaster layer comes to have reduced skin adhesive properties, so that peeling of the adhesive preparation from the skin occurs during application either partly at ends thereof or wholly; the blood level of the drug increases rapidly to produce severe side effects; and the adhesive preparation becomes more costly because the drug should be incorporated into a pressure-sensitive adhesive in an amount larger than the drug amount to be absorbed percutaneously. Thus, those expedients are not necessarily the best means.

SUMMARY OF THE INVENTION

Under these circumstances, the present inventors made intensive studies in order to develop a percutaneous absorption preparation capable of retaining a pharmacological effect over a prolonged time period regardless of the saturation solubility of tulobuterol in pressure-sensitive adhesives. As a result, it has been found that speedy percutaneous tulobuterol absorption and a satisfactory efficacy duration can be attained by incorporating dissolved tulobuterol and crystalline tulobuterol in a well balanced proportion into a pressure-sensitive adhesive. The present invention has been achieved based on this finding.

The percutaneous absorption preparation of the present invention comprises a support and, formed on one side thereof, a plaster layer comprising a pressure-sensitive adhesive and tulobuterol in an amount not lower than its saturation solubility in the pressure-sensitive adhesive, the tulobuterol contained in the plaster layer consisting of dissolved tulobuterol and crystalline tulobuterol with the ratio of the content of the crystalline tulobuterol to that of the dissolved tulobuterol being from 0.1 to 10. The ratio is obtained from the content of crystalline tulobuterol determined by X-ray crystallographic analysis and the content of dissolved tulobuterol calculated by subtracting the content of crystalline tulobuterol from the content of all the tulobuterol in the plaster layer.

DETAILED DESCRIPTION OF THE INVENTION

The tulobuterol contained in the plaster layer in the present invention, which is a drug having a pharmacological effect, is present therein in a crystalline state or dissolved state. The concentration of the dissolved tulobuterol directly influences the rate of percutaneous absorption, and it decreases with percutaneous absorption. Since the excess tulobuterol resulting from tulobuterol incorporation in an amount larger than the saturation solubility of tulobuterol in the pressure-sensitive adhesive used is dispersed in the plaster layer as crystalline tulobuterol, the amount of dissolved tulobuterol which can be incorporated in the plaster layer is suitably determined depending on the pressure-sensitive adhesive used.

On the other hand, the crystalline tulobuterol dissolves into the plaster layer during application to thereby function to replenish the dissolved tulobuterol the amount of which has decreased due to absorption by the skin. As a result, a high rate of percutaneous absorption and an effective blood level are maintained over a prolonged time period.

In the percutaneous absorption preparation of the present invention, the lower limit of the ratio of the content of crystalline tulobuterol to the content of dissolved tulobuterol in the plaster layer is 0.1, preferably 0.2, more preferably 1, while the upper limit thereof is 10, preferably 9, more preferably 5. If the ratio is lower than 0.1, the efficacy duration is not sufficiently long. If it exceeds 10, since the plaster layer surface contains a large amount of precipitated crystalline tulobuterol, not only the amount of the dissolved tulobuterol which comes into contact with the skin surface is reduced, resulting in a reduced rate of percutaneous absorption, but also the skin adhesion force is lowered.

The content of all the tulobuterol, i.e., the dissolved tulobuterol and crystalline tulobuterol, in the plaster layer is suitably determined depending on the pressure-sensitive adhesive used. However, the content thereof is generally from 1 to 50% by weight, preferably from 5 to 20% by weight. If the content thereof is lower than 1%, there are cases where sufficient efficacy or sustained manifestation of efficacy cannot be expected. If it exceeds 50% by weight, any further improvement in efficacy and duration cannot be expected, and there results an unfavorable tendency that the adhesion of the plaster layer to the skin is reduced.

For maintaining a high rate of percutaneous absorption over a prolonged time period in the percutaneous absorption preparation of the present invention, it is desirable that the re-dissolution of the crystalline tulobuterol takes place speedily so as to compensate a decrease in the amount of dissolved tulobuterol as a result of percutaneous absorption. Specifically, the lower limit of the ratio of the rate of elimination of the crystalline tulobuterol from the plaster layer to the rate of elimination of all the tulobuterol from the plaster layer is preferably 0.1, more preferably 0.2, most preferably 0.4 or higher. If the elimination rate ratio is lower than 0.1, there is a possibility of exhibiting a poor efficacy duration, because the re-dissolution of crystalline tulobuterol is insufficient as compared with the decrease of dissolved tulobuterol amount as a result of percutaneous absorption. The upper limit of the elimination rate ratio is preferably 1. The crystalline tulobuterol preferably has a particle size of 25 µm or less.

The rate of elimination of all the tulobuterol from the plaster layer is calculated from the amount of the drug which has migrated to the skin during application, which amount is obtained by subtracting the amount of the drug remaining in the plaster layer after application from the amount of the drug contained in the plaster layer before application. On the other hand, the rate of elimination of the crystalline tulobuterol is calculated from results of X-ray crystallographic analyses performed before and after application.

The pressure-sensitive adhesive contained in the plaster layer is not particularly limited as long as the object of the present invention can be accomplished with the same. However, preferred examples thereof include pressure-sensitive rubber adhesives such as polyisobutylene/polybutene rubbers, styrene/diene/styrene block copolymers, styrene/butadiene rubbers, nitrile rubbers, chloroprene rubbers, vinylpyridine rubbers, polyisobutylene rubbers, butyl rubbers, and isoprene/isobutylene rubbers and acryl-based pressure-sensitive adhesives obtained by polymerizing at least 50% by weight alkyl (meth)acrylate. The pressure-sensitive rubber adhesives are more preferable, with polyisobutylene/polybutene rubbers based pressure-sensitive rubber adhesives being most preferable in terms of stability and release of the drug. A so-called butyl rubber comprising a polyisobutylene as the main component and an isoprene rubber may be used as a polyisobutylene-based pressure-sensitive adhesive; the object of the present invention can be sufficiently accomplished with this pressure-sensitive adhesive.

The plaster layer in the present invention comprises the above-described tulobuterol and pressure-sensitive adhesive as the main components. The plaster layer may further contain a thermoplastic resin or the like. In particular, in the case of using a polyisobutylene-based pressure-sensitive adhesive, the plaster layer desirably contains a thermoplastic resin. In the plaster layer containing a thermoplastic resin along with a polyisobutylene-based pressure-sensitive adhesive, the thermoplastic resin functions as a moderate obstacle to the diffusion and migration of the tulobuterol within the plaster layer to thereby enable the tulobuterol to be continuously and efficiently released from the plaster layer and percutaneously absorbed by the living body over long. Namely, by incorporating both a polyisobutylene-based pressure-sensitive adhesive and a thermoplastic resin into the plaster layer, excellent efficacy duration can be attained, i.e., an effective blood level can be maintained over long. As a result, the number of doses (the number of applications per unit time) can be reduced and, hence, skin irritation can be diminished.

Preferred examples of such a thermoplastic resin include ones which are in a crystalline state at ordinary temperature and have a softening point of from 50° to 250° C. Specific examples thereof include rosins and derivatives thereof and tackifier resins such as terpene resins, terpene-phenol resins, petroleumresins, alkylphenol resins, and xylene resins. These resins may be incorporated either alone or in combination of two or more thereof in an amount of 50% by weight or smaller, preferably from 5 to 40% by weight.

It should be noted that the incorporation of a mineral oil as a carrier for drug dissolution or release into the plaster layer, as in conventional adhesive preparations, is undesirable. The reasons for this are as follows. First, there is a fear that the long-termstability of the drug in the preparation may be impaired due to interaction between the drug and either the mineral oil or impurities contained in the mineral oil. Secondly, the use of a mineral oil, which is a liquid substance, as a carrier for the drug highly accelerates drug release from the plaster layer, and this may cause problems that a rapid increase in blood level results to produce severe side effects and that the long efficacy duration which is an advantage of adhesive preparations is lost.

The plaster layer having the above-described constitution generally has a thickness of from 20 to 100 µm, preferably from 20 to 50 µm, so as to withstand long-term adhesion to a skin surface.

The support for forming the plaster layer thereon is not particularly limited as long as the tulobuterol-containing plaster layer can be formed and supported on one side thereof. However, a substantially tulobuterol-impermeable support is usually employed. Especially preferred is a support which is pliable in such a degree that, when applied to a skin surface, it is capable of following the curvature or movement of the skin surface so as not to give a considerably uncomfortable feeling. Examples of the support include single-layer films, e.g., films of plastics such as polyethylene, polypropylene, polyesters, poly(vinyl acetate), ethylene/vinyl acetate copolymers, poly(vinyl chloride), and polyurethanes, foils of metals such as aluminum and tin, nonwoven fabrics, cloths, and paper, and laminated films obtained by laminating such single-layer films. The thickness of such a support is generally from 5 to 500 µm, preferably from 5 to 200 µm. That side of these supports on which the plaster layer is to be formed is preferably subjected to corona discharge treatment, plasma treatment, oxidation treatment, or the like in order to improve adherence to the plaster layer and anchoring effect.

The percutaneous absorption preparation of the present invention is obtained by forming the above-described plaster layer on one side of the above-described support. It is desirable that the exposed plaster layer surface be kept being covered and protected with a releasing liner until immediately before application to a skin surface. Examples of the releasing liner include a paper or plastic film each of which has been rendered releasable by coating with, e.g., a silicone resin or a fluororesin.

The percutaneous absorption preparation of the present invention can be produced by a known method. For example, a pressure-sensitive adhesive and tulobuterol in an amount larger than the saturation solubility thereof in the pressure-sensitive adhesive are homogeneously dissolved into a good solvent therefor, and this plaster solution is applied on one side of a support and dried (preferably at a temperature of 60° to 100° C.) to recrystallize the excess tulobuterol. As a result, a preparation in which crystalline tulobuterol is uniformly dispersed in the plaster layer can be obtained. Examples of the good solvent include hexane and toluene in the case of the pressure-sensitive rubber adhesives and ethyl acetate and toluene in the case of the acryl-based pressure-sensitive adhesives.

In the percutaneous absorption preparation of the present invention, since the ratio of the content of crystalline tulobuterol to the content of dissolved tulobuterol in the plaster layer is within a specific range, not only the dissolved tulobuterol is speedily absorbed percutaneously, but also the crystalline tulobuterol serves to compensate a decrease in dissolved tulobuterol amount to maintain a high rate of percutaneous absorption over a prolonged time period. Moreover, the percutaneous absorption preparation, when applied to a patient, gives a reduced uncomfortable feeling and diminished skin irritation to the patient and shows excellent skin adhesive properties.

The present invention will be explained below in more detail by reference to Examples and Experiment Example, but the invention should not be construed as being limited thereto. In the following Examples, all parts and percents are given by weight.

EXAMPLE 1

Into hexane were dissolved 28.5 parts of high-molecular polyisobutylene having a viscosity-average molecular weight of 990,000 ("VISTANEX MML-80" produced by EXXON CHEMICAL JAPAN LTD.), 43 parts of low-molecular polyisobutylene having a viscosity-average molecular weight of 60,000 ("HIMOL 6H" produced by NIPPON PETROCHEMICALS COMPANY LTD.), 8.5 parts of polybutene having a viscosity-average molecular weight of 1,260 ("HV-300" produced by NIPPON PETROCHEMICALS COMPANY LTD.), and 20 parts of an alicyclic petroleum resin having a softening point of 100° C. ("ARKON P-100" produced by ARAKAWA CHEMICAL INDUSTRIES LTD.). Thus, a polyisobutylene-based pressure-sensitive adhesive solution (solid concentration, 25%) was prepared.

Tulobuterol was added to this solution in such an amount as to give a plaster layer having a tulobuterol content of 10%. After this mixture was sufficiently stirred, it was applied on a releasing liner at a thickness of 20 μm on a dry basis and dried to form a plaster layer. A polyester film (thickness, 12 μm) was then laminated therewith as a support. This laminate was allowed to stand at room temperature for one week to obtain a percutaneous absorption preparation of the present invention.

In the percutaneous absorption preparation obtained, the plaster layer contained 4% dissolved tulobuterol, with the remainder of the tulobuterol in an amount of 6% being present as crystalline tulobuterol in a dispersed state within the plaster layer and on the surface thereof.

EXAMPLE 2

A percutaneous absorption preparation of the present invention was obtained in the same manner as in Example 1, except that tulobuterol was added and mixed in such an amount as to give a plaster layer having a tulobuterol content of 20%.

In the percutaneous absorption preparation obtained, the plaster layer contained 4% dissolved tulobuterol, with the remainder of the tulobuterol in an amount of 16% being present as crystalline tulobuterol in a dispersed state within the plaster layer and on the surface thereof.

EXAMPLE 3

A percutaneous absorption preparation of the present invention was obtained in the same manner as in Example 1, except that tulobuterol was added and mixed in such an amount as to give a plaster layer having a tulobuterol content of 44%.

In the percutaneous absorption preparation obtained, the plaster layer contained 4% dissolved tulobuterol, with the remainder of the tulobuterol in an amount of 40% being present as crystalline tulobuterol in a dispersed state within the plaster layer and on the surface thereof.

EXAMPLE 4

A percutaneous absorption preparation of the present invention was obtained in the same manner as in Example 1, except that tulobuterol was added and mixed in such an amount as to give a plaster layer having a tulobuterol content of 40%.

In the percutaneous absorption preparation obtained, the plaster layer contained 4% dissolved tulobuterol, with the remainder of the tulobuterol in an amount of 36% being present as crystalline tulobuterol in a dispersed state within the plaster layer and on the surface thereof.

EXAMPLE 5

A percutaneous absorption preparation of the present invention was obtained in the same manner as in Example 1, except that tulobuterol was added and mixed in such an amount as to give a plaster layer having a tulobuterol content of 4.4%.

In the percutaneous absorption preparation obtained, the plaster layer contained 4% dissolved tulobuterol, with the remainder of the tulobuterol in an amount of 0.4% being present as crystalline tulobuterol in a dispersed state within the plaster layer and on the surface thereof.

EXAMPLE 6

A mixture of 45 parts of 2-ethylhexyl acrylate, 25 parts of 2-methoxyethyl acrylate, and 30 parts of vinyl acetate was polymerized in ethyl acetate in an inert gas atmosphere to prepare an acrylic pressure-sensitive adhesive solution. Tulobuterol was added to and mixed with this solution in such an amount as to give a plaster layer having a tulobuterol content of 15%. Using this mixture, a percutaneous absorption preparation of the present invention was obtained in the same manner as in Example 1.

In the percutaneous absorption preparation obtained, the plaster layer contained 12.5% dissolved tulobuterol, with the remainder of the tulobuterol in an amount of 2.5% being present as crystalline tulobuterol in a dispersed state within the plaster layer and on the surface thereof.

EXAMPLE 7

Into hexane were dissolved 55 parts of high-molecular polyisobutylene having a viscosity-average molecular weight of 2,100,000 ("VISTANEX MML-140" produced by EXXON CHEMICAL JAPAN LTD.), 15 parts of low-molecular polyisobutylene having a viscosity-average molecular weight of 60,000 ("HIMOL 6H"), 10 parts of polybutene having a viscosity-average molecular weight of 1,260 ("HV-300"), and 20 parts of an alicyclic petroleum resin having a softening point of 100° C. ("ARKON P-100"). Thus, a polyisobutylene-based pressure-sensitive adhesive solution (solid concentration, 25%) was prepared.

Tulobuterol was added to and mixed with this solution in such an amount as to give a plaster layer having a tulobuterol content of 10%. Using this mixture, a percutaneous absorption preparation of the present invention was obtained in the same manner as in Example 1.

In the percutaneous absorption preparation obtained, the plaster layer contained 2% dissolved tulobuterol, with the remainder of the tulobuterol in an amount of 8% being present as crystalline tulobuterol in a dispersed state within the plaster layer and on the surface thereof.

EXAMPLE 8

Into hexane were dissolved 60 parts of high-molecular polyisobutylene having a viscosity-average molecular weight of 2,100,000 ("VISTANEX MML-140"), 15 parts of low-molecular polyisobutylene having a viscosity-average molecular weight of 60,000 ("HIMOL 6H"), 10 parts of polybutene having a viscosity-average molecular weight of 1,260 ("HV-300"), and 30 parts of an alicyclic petroleum resin having a softening point of 100° C. ("ARKON P-100"). Thus, a polyisobutylene-based pressure-sensitive adhesive solution (solid concentration, 25%) was prepared.

Tulobuterol was added to and mixed with this solution in such an amount as to give a plaster layer having a tulobuterol content of 10%. Using this mixture, a percutaneous absorption preparation of the present invention was obtained in the same manner as in Example 1.

In the percutaneous absorption preparation obtained, the plaster layer contained 1.5% dissolved tulobuterol, with the remainder of the tulobuterol in an amount of 8.5% being present as crystalline tulobuterol in a dispersed state within the plaster layer and on the surface thereof.

COMPARATIVE EXAMPLE 1

A percutaneous absorption preparation was obtained in the same manner as in Example 1, except that tulobuterol was added and mixed in such an amount as to give a plaster layer having a tulobuterol content of 50%.

In the percutaneous absorption preparation obtained, the plaster layer contained 4% dissolved tulobuterol, with the remainder of the tulobuterol in an amount of 46% being present as crystalline tulobuterol in a dispersed state within the plaster layer and on the surface thereof.

COMPARATIVE EXAMPLE 2

A percutaneous absorption preparation was obtained in the same manner as in Example 1, except that tulobuterol was added and mixed in such an amount as to give a plaster layer having a tulobuterol content of 4.2%.

In the percutaneous absorption preparation obtained, the plaster layer contained 4% dissolved tulobuterol, with the remainder of the tulobuterol in an amount of 0.2% being present as crystalline tulobuterol in a dispersed state within the plaster layer and on the surface thereof.

EXPERIMENT EXAMPLE 1

The percutaneous absorption preparations obtained in the Examples and Comparative Examples given above were examined for skin adhesive property and for blood level change with time after administration to rabbits. The results obtained are shown in Tables 1 and 2.

The rate of elimination of all the tulobuterol in each plaster layer was determined by subtracting the amount of the drug remaining in the plaster layer at each of 3, 6, 12, and 24 hours after application from the amount of the drug contained in the plaster layer before application to obtain drug release rates for 0–6 hours, 6–12 hours, and 12–24 hours, respectively, and averaging these release rates.

TABLE 1

| Sample No. | Content Ratio (crystalline /dissolved) | Total Content (wt %) | Ratio of Elimination Rate (crystalline /all) | Skin Adhesive Property* 0 hr | 24 hr |
|---|---|---|---|---|---|
| Example 1 | 1.5 (6/4) | 10 | 0.53 | A | A |
| Example 2 | 4.0 (16/4) | 20 | 0.69 | A | A |
| Example 3 | 10.0 (40/4) | 44 | 0.45 | A | B |
| Example 4 | 9.0 (36/4) | 40 | 0.47 | A | B |
| Example 5 | 0.1 (0.4/4) | 4.4 | 0.60 | A | A |
| Example 6 | 0.2 (2.5/12.5) | 15 | 0.88 | A | A |
| Example 7 | 4.0 (8/2) | 10 | 0.16 | A | A |
| Example 8 | 5.7 (8.5/1.5) | 10 | 0.07 | A | A |
| Comparative Example 1 | 11.5 (46/4) | 50 | 0.30 | B | C |
| Comparative Example 2 | 0.05 (0.2/4) | 4.2 | 0.68 | A | A |

*Each preparation sample cut into a size of 10 cm² was applied to the chest of a human being, and the skin adhesive properties thereof immediately after application and at 24 hours after application were evaluated based on the following criteria.
A: suffered almost no end peeling.
B: suffered end peeling.
C: peeled off during application.

As Table 1 shows, the percutaneous absorption preparations of Examples 1 to 8 did not peel off in 24-hour application and mostly exhibited excellent skin adhesive properties, although some of these suffered end peeling.

In contrast, the percutaneous absorption preparation of Comparative Example 1, in which the ratio of the content of crystalline tulobuterol to the content of dissolved tulobuterol was 11.5, suffered end peeling and peeled off during application.

TABLE 2

| | Blood Level** (ng/ml) | | | | |
|---|---|---|---|---|---|
| Sample No. | 2 hr | 4 hr | 6 hr | 8 hr | 24 hr |
| Example 1 | 51.6 | 22.7 | 17.5 | 12.3 | 8.6 |
| Example 2 | 53.8 | 29.0 | 23.6 | 19.9 | 14.4 |

TABLE 2-continued

| Sample No. | Blood Level** (ng/ml) | | | | |
|---|---|---|---|---|---|
| | 2 hr | 4 hr | 6 hr | 8 hr | 24 hr |
| Example 3 | 47.0 | 30.6 | 27.9 | 21.1 | 12.8 |
| Example 4 | 48.3 | 30.2 | 27.1 | 22.7 | 15.0 |
| Example 5 | 31.5 | 17.1 | 10.8 | 7.7 | 2.0 |
| Example 6 | 60.1 | 36.9 | 24.6 | 13.7 | 8.1 |
| Example 7 | 34.8 | 18.6 | 12.1 | 8.9 | 2.2 |
| Example 8 | 31.3 | 16.7 | 10.9 | 5.9 | 1.6 |
| Comparative Example 1 | 16.5 | 9.0 | 3.1 | 2.3 | 1.3 |
| Comparative Example 2 | 28.9 | 10.5 | 4.0 | 1.9 | not detected |

**Each preparation sample cut into a size of 20 cm$^2$ was applied to the back of a depilated rabbit, and the blood thereof was sampled with the lapse of time to determine the amount of tulobuterol contained in the plasma by gas chromatography.

As Table 2 shows, the percutaneous absorption preparations of Examples 1 to 8 were satisfactory in that a speedy increase in blood level in the initial stage after application was attained and tulobuterol was present in the plasma even after 24 hours.

In contrast, the percutaneous absorption preparation of Comparative Example 2, in which the ratio of the content of crystalline tulobuterol to the content of dissolved tulobuterol was 0.05, was so poor in efficacy duration that tulobuterol was not detected in the plasma at 24 hours after application.

The percutaneous absorption preparation of Example 8, in which the ratio of the rate of elimination of crystalline tulobuterol to the rate of elimination of all the tulobuterol was 0.07, was slightly poorer in efficacy duration than the percutaneous absorption preparations of the other Examples.

According to the percutaneous absorption preparation of the present invention, tulobuterol is percutaneously absorbed efficiently without taking an expedient such as increasing the thickness of the plaster layer containing tulobuterol dissolved therein, heightening the content of tulobuterol, or enlarging the area in which the plaster layer is in contact with the skin. Hence, the percutaneous absorption preparation of the invention, when applied to a patient, not only gives a reduced uncomfortable feeling and diminished skin irritation to the patient, but also suffers neither end peeling nor peeling off both caused by deterioration of skin adhesive properties. In this percutaneous absorption preparation, severe side effects of the drug caused by a rapid increase in blood level of the drug are prevented. The percutaneous absorption preparation is also excellent in cost because there is no need of incorporating the drug into the plaster layer in an excess amount.

Furthermore, since tulobuterol is continuously and efficiently released from the plaster layer and percutaneously absorbed by the living body over a prolonged time period, a satisfactory efficacy duration can be attained, i.e., an effective blood level can be maintained over long. In addition, since the number of doses (the number of applications per unit time) can be reduced, skin irritation can be diminished.

While the invention has been described in detail and with reference to specific embodiments thereof, it will be apparent to one skilled in the art that various changes and modifications can be made therein without departing from the spirit and scope thereof.

What is claimed is:

1. A percutaneous absorption preparation comprising a support and, formed on one side thereof, a plaster layer comprising a pressure-sensitive adhesive and tulobuterol in an amount not lower than its saturation solubility in the pressure-sensitive adhesive, said tulobuterol contained in the plaster layer consisting of dissolved tulobuterol and crystalline tulobuterol with the ratio of the content of the crystalline tulobuterol to that of the dissolved tulobuterol being from 0.1 to 10.

2. The percutaneous absorption preparation of claim 1, wherein the ratio of the rate of elimination of the crystalline tulobuterol from the plaster layer to the rate of elimination of all the tulobuterol from the plaster layer is from 0.1 to 1.

3. The percutaneous absorption preparation of claim 1, wherein the content of all the tulobuterol is 1 to 50% by weight based on the weight of the plaster layer.

4. The percutaneous absorption preparation of claim 1, wherein the plaster layer has a thickness of 20 to 100 μm.

5. A tulobuterol administration method, comprising at least the following steps:

(a) providing a support for a percutaneous absorption preparation, and, forming on one side of the support, a plaster layer comprising a pressure-sensitive adhesive and an amount of tulobuterol not lower than its saturation solubility in the pressure-sensitive adhesive;

(b)
 (i) measuring the tulobuterol, using X-ray crystallography, to give a crystalline tulobuterol amount,
 (ii) obtaining a dissolved tulobuterol amount by subtracting the measured crystalline tulobuterol amount of (b)(i) from the tulobuterol amount of (a); and,
 (iii) determining a ratio of the crystalline tulobuterol amount of (i) to the dissolved tulobuterol amount of (ii); and, (c) administering to a patient a preparation according to (a) wherein said preparation has a ratio according to (b)(iii) in a range of 0.1 to 10.

6. A method of constructing a tulobuterol absorption preparation, comprising at least the steps of:

(a) providing a support for a percutaneous absorption preparation, and, forming on one side of the support, a plaster layer comprising a pressure-sensitive adhesive and an amount of tulobuterol not lower than its saturation solubility in the pressure-sensitive adhesive;

(b)
 (i) measuring the tulobuterol, using X-ray crystallography, to give a crystalline tulobuterol amount,
 (ii) obtaining a dissolved tulobuterol amount by subtracting the measured crystalline tulobuterol amount of (b)(i) from the tulobuterol amount of (a); and,
 (iii) determining a ratio of the crystalline tulobuterol amount of (i) to the dissolved tulobuterol amount of (ii); and, (c) providing the preparation of (a) with the ratio according to (b)(iii) in a range of 0.1 to 10.

* * * * *